United States Patent

Yamazaki et al.

Patent Number: 5,142,140
Date of Patent: Aug. 25, 1992

[54] APPARATUS FOR COUNTING PARTICLES SUSPENDED IN A FLUID HAVING A POLARIZING BEAM SPLITTER

[75] Inventors: Isao Yamazaki, Niihari; Hiroshi Ohki, Tsuchiura; Toshio Kaneko; Keiji Kataoka, both of Katsuta, all of Japan

[73] Assignee: Hitachi, Ltd., Tokyo, Japan

[21] Appl. No.: 603,290

[22] Filed: Oct. 25, 1990

[30] Foreign Application Priority Data

Oct. 26, 1989 [JP] Japan ............................... 1-279487

[51] Int. Cl.⁵ .............................................. G01V 9/04
[52] U.S. Cl. .................................. 250/222.2; 250/574; 356/338
[58] Field of Search ............... 250/222.2, 225, 574; 356/337, 338, 341, 73

[56] References Cited

U.S. PATENT DOCUMENTS

| | | | |
|---|---|---|---|
| 3,612,688 | 10/1971 | Liskowitz | 250/225 |
| 4,072,421 | 2/1978 | Coyne et al. | 250/222.2 |
| 4,548,499 | 10/1985 | Eisert et al. | |
| 4,572,676 | 2/1986 | Biermans et al. | 250/225 |
| 4,636,075 | 1/1987 | Knollenberg | |

FOREIGN PATENT DOCUMENTS 0359681 3/1990 European Pat. Off. .
90/0477 5/1990 PCT Int'l Appl. .

Primary Examiner—David C. Nelms
Assistant Examiner—T. Davenport
Attorney, Agent, or Firm—Antonelli, Terry, Stout & Kraus

[57] ABSTRACT

An apparatus for counting and analyzing sample particles such as cells suspended in a fluid by applying an irradiation beam such as a laser beam to the sample particles in a flow cell. The apparatus includes a device for supplying a flow cell with suspension of sample particles, an optical system for applying a laser beam to the sample particles in the above-mentioned suspension, a light gathering device for forming image of the above-mentioned sample particles, a light sensing device for sensing light from the above-mentioned formed image of the sample particles, and an analysis for analyzing the above-metnioned sample particles on the basis of the above-mentioned sensed light. The optical system may include a polarizing beam splitter and such convergent lenses having mutually different magnifications relative to two directions perpendicular to the optical axis of the laser beam.

20 Claims, 3 Drawing Sheets

APPARATUS FOR COUNTING PARTICLES SUSPENDED IN A FLUID HAVING A POLARIZING BEAM SPLITTER

BACKGROUND OF THE INVENTION

The present invention relates to an apparatus for analyzing the nature of particles by causing them to flow, and is particularly concerned with an apparatus efficient for an analysis of flowing cells such as the classification of leukocytes.

An example in which the above-noted particles are cells will be taken in the description below.

One of the conventional methods of distinguishing sample particles in a suspension is flow cytometry. In this method, cells in a suspension, typically a blood sample, are run through the minute passage of a flow cell, where each particle in the blood sample is illuminated by one or more beams of light in the sensing zone. Then, the result of the interaction of a light beam or a group of light beams on each particle is sensed by one or more light sensors. Interaction here means a phenomenon such as the occurrence of fluorescence from particles caused by light beams scattered by particles. Conventionally, light sensors are designed so that they can measure scattered light at a particular scattering angle or fluorescence having a particular wavelength. In this way, each particle flowing through the flow cell is characterized by scattered light, fluorescence or one or more other optical or electrical characteristics. According to these characteristics, each particle is mapped in a specific space based on radiation intensity or another characteristics such as red or green which is measured by the sensor. It has been desired to map different kinds of particles in a sample in correspondingly different areas in the specific space so that the type of each particle (e.g. cell) can be estimated from their mapping in the specific space. Therefore, to improve accuracy of the analysis of particles, the sheath flow method has been employed for causing flow in the flow cell. In this method, a blood sample flows only in the center of the minute passage. Furthermore, a light beam of a substantially elliptical shape whose major axis is perpendicular to the direction of the flow in the flow cell is used so that the quantity of light each particle receives can be uniform. Japanese Unexamined Patent Application Publication (Kokai) No. 63-47635 discloses means for scanning a laser beam perpendicularly to the direction of the stream in the flow cell in order to expand the area in which the quantity of light is uniform.

As the rate of the flow of a sample increases, the position of each cell flowing through the flow cell varies more greatly. Unless the quantity of laser light is uniform in the area where particles pass, the analysis will be less accurate, because the intensity of scattered light or fluorescence from particles depends on the quantity of laser light. The quantity of laser light in the area where particles pass needs to be uniform. The laser for use in flow cytometry produces a Gaussian beam whose quantity of light is large in the center and small in the periphery.

The above-mentioned conventional techniques have enlarged the width of a laser beam into an elliptical shape to use the center where the quantity of the light is uniform. Such a laser beam has caused energy loss, so a powerful, and thus large, laser has been necessary for these techniques. However, a large laser leads to a large size of the entire equipment which costs much more. Moreover, these techniques have drawbacks such as the heat and vibration from lasers which lower their reliability and shorten their life. Besides, the section of the sample flow in the flow cell must be small because of the narrow range where the quantity of light is uniform. This has prevented the flow of the sample from being enlarged, necessitating a long period of time for analysis.

When a laser beam perpendicular to the direction of the stream in the flow cell, it is necessary to apply a uniform radiation intensity of the laser to the range where cells move during laser scanning. The laser beam must be expanded in the direction of the stream in the flow cell, which leads to a large loss of laser energy.

SUMMARY OF THE INVENTION

The present invention relates to an apparatus for counting and analyzing sample particles suspended in a fluid, particularly an efficient apparatus for flow cytometry for producing an irradiation beam whose range of uniform quantity of light is enlarged by a polarizing beam splitter without the light source itself enlarging the width of the beam so as to allow the use of a small-sized light source like a laser and to ensure the small size and high reliability of the entire apparatus.

An apparatus for flow cytometry in accordance with the present invention includes for instance, a fluid supplying means for supplying a flow cell with the suspension of sample particles, an optical means for applying a laser beam to sample particles in the suspension, a light gathering means for forming the image of the sample particles, a light sensing mean for sensing light coming from the focused image of the sample particles, and an analysis means for analyzing the sample particles by using the sensed light. The optical means includes a polarizing beam splitter disposed in the path of a laser beam, and convergent lenses whose magnification is different in two directions perpendicular to the optical axis of the laser.

DETAILED DESCRIPTION OF THE PREFERRED EMBODIMENT

Figure 1:
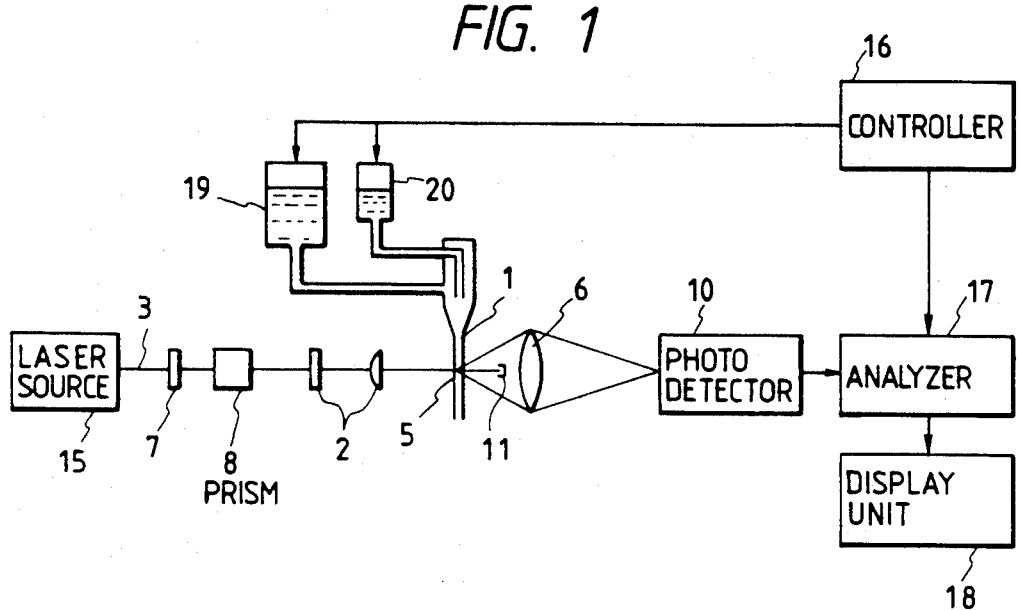
FIG. 1 is a schematic composition of an embodiment of the present invention.

In a flow cytometry apparatus in accordance with the present invention, a laser beam is divided by a polarized beam splitter into two orthogonal polarizing components diverging by an angle of a minute degree from each other. Each component is focused to form a spot in a flow cell by light gathering lenses whose magnification is different in two directions perpendicular to the optical axis of the laser, but the two components have their spots at a minute distance from each other. The distance depends on the diverging angle of the polarizing beam splitter and on the focal length of the light gathering lenses, but as long as the distance is such that the spots overlap, the quantity of the light will be uniform in the range between the adjacent spots. Therefore, the rate of the flow of the sample can be increased and the time for the analysis of cells can be decreased. In addition, the range of uniform quantity of light can be provided without enlarging the width of the laser beam at its light source, so the laser beam has a smaller energy loss. Therefore, a small output laser can be used as the light source with the result that the entire apparatus can be small-sized and highly reliable.

Further reduction of energy loss is possible by using more than one polarizing beam splitter to provide many spots at equal intervals along a line for further enlarging the range of uniform quantity of light. In this case, polarizing beam splitters are placed on the optical axis with a polarization rotator between adjacent polarizing beam splitters. When the laser beam in use is one whose two orthogonal polarized components from a polarizing beam splitter are the same percentage, the laser beam is divided by the first polarizing beam splitter into two laser beams having the same intensity. The two laser beams each have only one half of the orthogonal polarized component, but they are rotated by the polarization rotator so that their two orthogonal polarized components from a polarizing beam splitter can be the same percentage again. Then, the two laser beams are divided by the second polarizing beam splitter into four laser beams having the same intensity. Repeating the above-mentioned process obtains many laser beams having the same intensity. On the other hand, given that the smallest diverging angle is $\theta_d$, the diverging angle that the orthogonal polarized components provided by each polarizing beam splitter has will be $2\theta_d$, $4\theta_d$ and so on. Then, in the case where the first polarizing beam splitter has the diverging angle $2\theta_d$ and the second one the diverging angle $\theta_d$, the laser beam is divided at an angle of $2\theta_d$ by the first polarizing beam splitter and broken up further an angle of $\theta_d$ by the second polarizing beam splitter, resulting in four laser beams separated by the same angle $\theta_d$. Many such laser beams with the same intensity at the same angle relative to adjacent laser beams are focused in the flow cell by convergent lenses, resulting in many spots disposed at the same interval along a line. Laser beams at the same angle relative to adjacent laser beams can be obtained no matter in what order two or more polarizing beam splitters may be placed. However, placing the polarizing beam splitter having the smallest diverging angle nearest to the flow cell allows adjacent spots to have mutually orthogonal polarized components. Since mutually orthogonal polarized components do not interfere with each other, there is no possibility of the quantity of light lacking uniformity due to the interference of adjacent spots with each other.

Referring first to FIG. 1, there is shown the composition of the principal part of a flow cytometry apparatus which is the first embodiment of the present invention. On the extension of a laser beam 3 emitted from the laser light source 15 are a ½ wave plate 7, a Wollaston prism 8, convergent lenses 2, a flow cell 1, a beam trap 11, light gathering lenses 6 and light sensor 10. The flow cell 1 is supplied with a sheath fluid by the means 19 for providing a sheath fluid and with a suspension of sample particles by a sample provision means 20. The light sensor 10 is connected to an analyzer 17, which is connected to a display unit 18. A controller 16 is connected to the analyzer 17, the sheath fluid provision means 19 and the sample provision means 20.

The laser beam 3 travels though the light beam forming means composed of the ½ wave plate 7, Wollaston prism 8 and convergent lenses 2, comes to the observation point 5 on the axis of the flow cell 1 and is absorbed by the beam trap 11 provided beyond the observation point 5. When a suspension of cells is run through the flow cell 1 in the form of a sheath flow, light is emitted from cells at the observation point 5. The abovementioned light emitted at the observation point 5 is focused on the sensing surface of the light sensor 10 and is then sensed with respect to intensity. The light sensed by the light sensor 10 is scattered light or fluorescence emitted from the cells, so it is closely related to the type and nature of the cells. Therefore, by sensing and analyzing the scattered light and fluorescence from each cell it is possible to find out the number or ratio of each of various kinds of cells in a blood sample.

Figure 2:
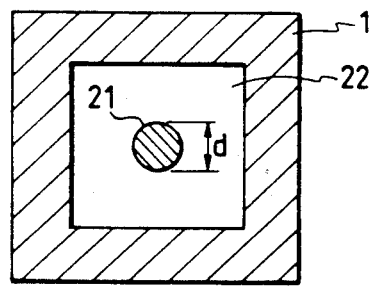
FIG. 2 is a sectional view of the flow in a flow cell.

FIG. 2 is a sectional side view of the flow cell 1. In the portion measuring d in diameter flows a sample 21 which is a suspension of sample particles, and around it a sheath fluid 22, both forming a sheath flow. To shorten the time for the analysis, it is necessary to increase the rate of the sample flow. However, increasing the rate leads to the enlargement of the diameter d of the sample 21. For highly accurate analysis, the radiation intensity of a laser beam needs to be uniform and also higher than a certain level in the area of the sample 21.

Figure 3:
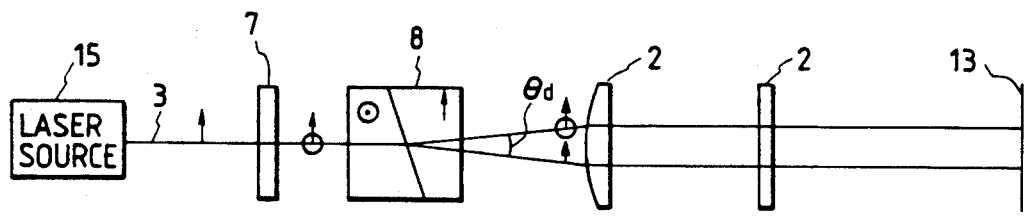
FIG. 3 is a schematic view illustrating the operation of the above first embodiment.

FIG. 3 is an illustration of the operation of the light beam forming means in the embodiment shown in FIG. 1. Generally, before the light beam forming means (left of the means in the figure), the plane of polarization for the laser beam 3 is vertical or horizontal. The ½ wave plate 7 changes the plane of polarization into a plane tilted 45° from the horizontal to provide the laser beam with both vertical and horizontal polarized components. Then, the laser beam 3 is divided by the Wollaston prism 8 into two orthogonal polarized components. The convergent lenses 2 are composed of cylindrical lenses which converge the two components of the laser beam on two points adjacent to each other on the convergence plane 13, each of them forming an elliptical spot.

Figure 4:
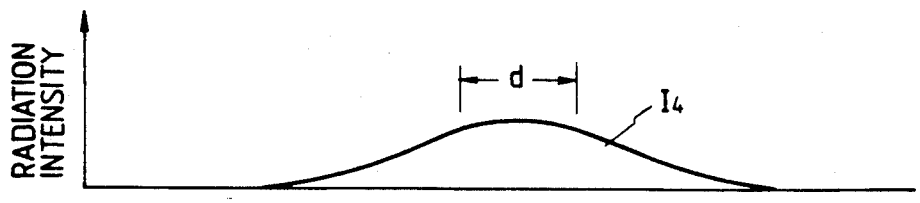
FIG. 4 is a graphical representation of the distribution of the radiation intensity of a laser beam at the observation point in a conventional apparatus.

FIG. 4 is a graph showing the distribution of the radiation intensity of a laser beam at the observation point of conventional apparatuses. The spot of the laser beam is shaped like a horizontally long ellipse so that the radiation intensity can be uniform inside the sectional area of the sample 21 measuring d in diameter.

Figure 5:
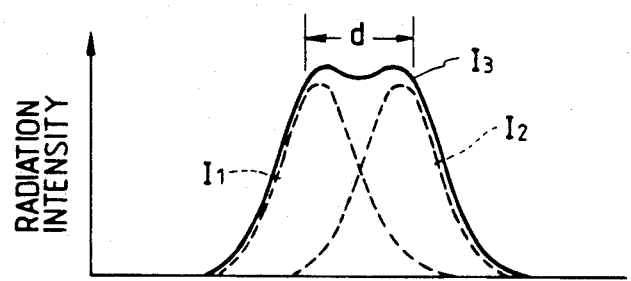
FIG. 5 is a graphical representation of the distribution of the radiation intensity of a laser beam at the observation point in the above first embodiment.

FIG. 5 is a graph showing the distribution of the radiation intensity of a laser beam at the observation point 5 of the embodiment shown in FIG. 1. The radiation intensity for one of the two spots is denoted by the broken line $I_1$ and that for another by $I_2$. The synthesized radiation intensity is denoted by the solid line $I_3$. The radiation intensity is almost uniformly distributed in the range where the two spots overlap each other. Therefore, since the uniformity of the radiation intensity distribution can be achieved despite the narrowness of the width of each spot, the greater part of the energy of the laser beam is concentrated inside the sectional area measuring d in diameter, so this allows a higher energy density than the conventional apparatuses do as shown in FIG. 4. Therefore, only a small output laser light source is sufficient for obtaining the energy density required for the analysis of particles.

In addition to the above, the wide range of uniform radiation intensity provides the ability to enlarge the sectional area of the flow of the sample suspension of cells and thus to increase the rate of the flow of the suspension, which then leads to the shortening of the time for the analysis.

Furthermore, since in this embodiment each of the two spot beams converged by the convergent lenses 2 is of a substantially elliptical shape whose major axis is perpendicular to the direction of the stream, the observation point is short in the direction of the stream, which lessens the time for a cell to pass the observation point and thus shortens the time for the analysis. The length of a spot in the above-mentioned direction of the stream can be changed by adjusting the focal length of one of the cylindrical lenses composing the convergent lenses 2 without altering the distribution of the radiation intensity perpendicular to the above-mentioned direction of the stream.

Figure 6:
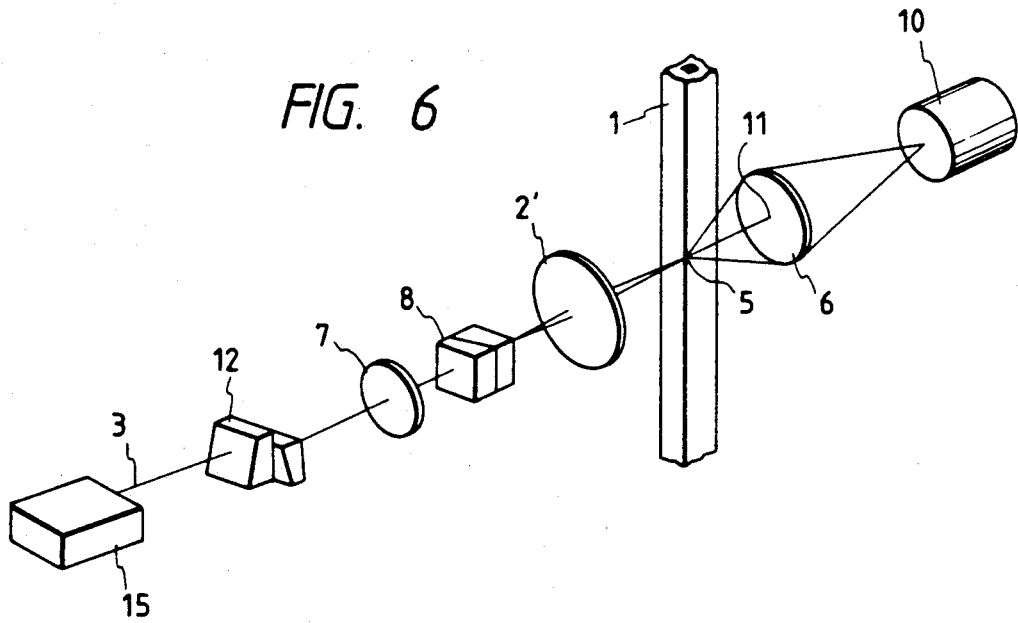
FIG. 6 is a schematic composition of another embodiment of the present invention.

FIG. 6 is a schematic composition of the principal part of a flow cytometry apparatus which is another embodiment of the present invention. The difference from the embodiment shown in FIG. 1 lies in the use of spherical lens 2' in place of the cylindrical lenses 2 in FIG. 3, and in the mounting of beam shaping prisms 12 on the optical axis of the laser beam 3. The laser beam 3 is formed into a beam of a vertically long elliptical shape by the beam shaping prisms 12. Then, the beam travels through the ½ wave plate 7 and the Wollaston prism 8 and is converged on the observation point 10 by the convergent lens 2, so that it becomes a spot of a substantially elliptical shape whose major axis is perpendicular to the direction of the stream as in the embodiment in FIG. 1. In contrast to the embodiment in FIG. 1, this second embodiment does not use cylindrical lenses, so the whole apparatus can be less expensive, and the use of a spherical lens instead of such cylindrical lenses facilitates checking and adjustment.

Figure 7:
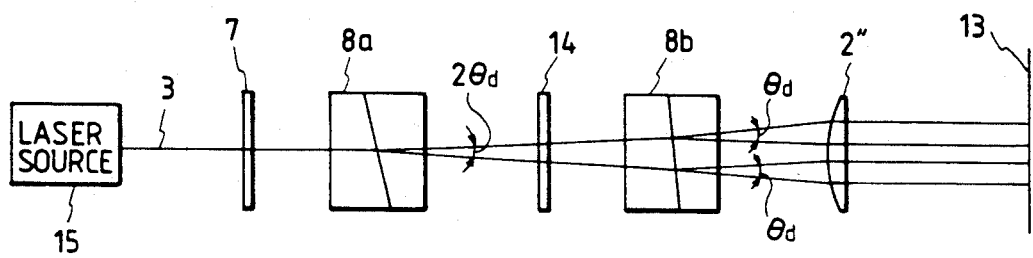
FIG. 7 is a schematic composition of the principal part of a third embodiment of the present invention.

FIG. 7 is a view showing the operation of the means for forming light beams in a third embodiment of the present invention. This embodiment uses Wollaston prisms 8a and 8b and a ¼ wave plate 14 between them. Before entering the means for forming light beams, the laser beam 3 generally has a vertical or horizontal plane of polarization. The ½ wave plate 7 changes the plane of polarization into one tilted 45° from the horizontal in order for the laser beam to have both vertical and horizontal polarizing components. Then, the laser beam 3 is divided by the Wollaston prism 8a into two orthogonal polarized components. Each of the two polarized components is formed by the ¼ wave plate 14 into circularly polarized light. The two components are then divided by the Wollaston prism 8b into four orthogonal polarized components. The four laser beams 3' are converged by a convergent lens 2" on the convergence plane 13 along a line, each forming a circular spot. In this case, the Wollaston prism 8a has a diverging angle specified as $2\theta_d$ relative to the diverging angle $\theta_d$ of the Wollaston prism 8b, so the four beams from the Wollaston prism 8b are directed with the angle $\theta_d$ relative to each other, resulting in equal distances between their spots on the convergence plane 13. Since the four beams produced by the Wollaston prism 8b have orthogonal polarized components, the polarized component of each beam is orthogonal to the polarized components of the adjacent beams such that no interference occurs.

Figure 8:
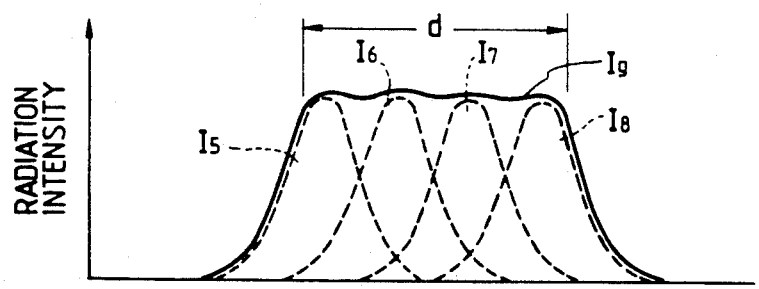
FIG. 8 is a graphical representation of the distribution of the radiation intensity of a laser beam at the observation point of the above third embodiment.

FIG. 8 is a graph showing the distribution $I_9$ of the radiation intensity of a laser beam on the convergence plane 13 in the embodiment shown in FIG. 7. Since the range where the spots $I_5$ to $I_8$ overlap has an almost uniform radiation intensity, the intensity of the scattered light and the fluorescence from the cells do not vary no matter where they may pass within the range, which allows accurate analysis. In this embodiment, the range of uniform radiation intensity is wider than in the other embodiments, so this embodiment is capable of providing higher energy efficiency. In addition, the capability of providing a radiation range whose size perpendicular to the direction of the stream, is smaller than its horizontal size in the direction of the stream without the use of cylindrical lenses or beam shaping prisms facilitates checking and adjustment.

It is possible to increase the number of Wollaston prisms in order to have more overlapping spots. In this case, as long as a polarizing beam splitter having the smallest diverging angle is placed nearest to the flow cell, the other polarizing beam splitters can be placed in any order. On the other hand, a ¼ wave plate is used for the polarization rotator in the third embodiment, but a ½ wave plate or a polarizing plate can be used to obtain the same effect. Wollaston prisms are used as polarizing beam splitters in the above embodiments, but Rochon prisms or Senarmont prisms can be used for the same purpose.

The above description has related to the use of a fluid as the carrier of sample particles. However, it will be obvious to those skilled in the art that not only a fluid but other forms of matter such as a gas can be used as the above-mentioned carrier if they are suitable for the above purpose.

According to the present invention, it is possible for a laser light source in a flow cytometry apparatus to provide a range of uniform radiation intensity without enlarging the width of the laser beam because the beam can be broken up into more than one beam by polarizing beam splitters and converged as more than one spot along a line on the observation point in the flow cell. Therefore, embodiments in accordance with the present invention allow the use of a small output laser as their light source, thus as a whole being low-cost and high-reliability flow cytometry apparatuses.

What is claimed is:

1. An apparatus for counting particles suspended in a fluid, comprising:
   a flow cell;
   fluid supplying means for supplying said flow cell with a fluid containing sample particles;
   optical means for applying an irradiation beam to said sample particles in said fluid;
   light gathering means for forming an image of the sample particles;
   light sensing means for sensing light from the formed image of the sample particles; and
   analyzing means for analyzing said sample particles on the basis of the sensed light;
   wherein the optical means includes at least one polarizing beam splitter.

2. An apparatus for counting particles suspended in a fluid, comprising:
   a flow cell;

fluid supplying means for supplying said flow cell with a fluid containing sample particles;

optical means for applying an irradiation beam to said sample particles in said fluid;

light gathering means for forming an image of the sample particles;

light sensing means for sensing light from the formed image of the sample particles; and analyzing means for analyzing said sample particles on the basis of the sensed light;

wherein said optical means includes at least one polarizing beam splitter, and two convergent lenses having mutually different magnifications with respect to two directions perpendicular to an optical axis of said irradiation beam, said two convergent lenses being disposed between said at least one polarizing beam splitter and said flow cell.

3. An apparatus for counting particles suspended in a fluid according to claim 1, wherein each polarizing beam splitter of said at least one polarizing beam splitter is one of a Wollaston prism, a Rochon prism, and a Senarmont prism.

4. An apparatus for counting particles suspended in a fluid according to claim 1, wherein said optical means includes a plurality of polarizing beam splitters.

5. An apparatus for counting particles suspended in a fluid according to claim 1, wherein said optical means includes a plurality of polarizing beam splitters and at least one polarization rotator disposed such that a polarization rotator is disposed between adjacent ones of said plurality of polarizing beam splitters.

6. An apparatus for counting particles suspended in a fluid according to claim 5, wherein one of said plurality of polarizing beam splitters which is disposed nearest to said flow cell has a smallest diverging angle among said plurality of polarizing beam splitters.

7. An apparatus for counting particles suspended in a fluid according to claim 1, wherein said irradiation beam is a laser beam.

8. An apparatus for counting particles suspended in a fluid according to claim 1, wherein said fluid is a suspension.

9. An apparatus for counting particles suspended in a fluid according to claim 1, wherein said irradiation beam is a laser beam and said fluid is a suspension.

10. An apparatus for counting particles suspended in a fluid according to claim 7, wherein each polarizing beam splitter of said at least one polarizing beam splitter is one of a Wollaston prism, a Rochon prism, and a Senarmont prism.

11. An apparatus for counting particles suspended in a fluid according to claim 7, wherein said optical means includes a plurality of polarizing beam splitters.

12. An apparatus for counting particles suspended in a fluid according to claim 7, wherein said optical means includes a plurality of polarizing beam splitters and at least one polarization rotator disposed such that a polarization rotator is disposed between adjacent ones of said plurality of polarizing beam splitters.

13. An apparatus for counting particles suspended in a fluid according to claim 7, wherein said optical means includes a laser light source, a $\frac{1}{2}$ wave plate, a Wollaston prism, and a light gathering lens disposed in the order listed prior to said flow cell.

14. An apparatus for counting particles suspended in a fluid according to clam 7, wherein said light gathering means includes a light gathering lens, and said light sensing means includes a light sensor.

15. An apparatus for counting particles suspended in a fluid according to claim 7, wherein said optical means includes a laser light source, a $\frac{1}{2}$ wave plate, a Wollaston prism, and a light gathering lens disposed in the order listed prior to said flow cell, and said light gathering means includes a light sensor.

16. An apparatus for counting particles suspended in a fluid according to claim 7, wherein said optical means further includes beam shaping prisms disposed prior to said at least one polarizing beam splitter and a spherical lens disposed between said at least one polarizing beam splitter and said flow cell.

17. An apparatus for counting particles suspended in a fluid according to claim 7, wherein said optical means includes a laser light source, beam shaping prisms, a $\frac{1}{2}$ wave plate, a Wollaston prism, and a spherical lens disposed in the order listed prior to said flow cell.

18. An apparatus for counting particles suspended in a fluid according to claim 7, wherein said optical means includes a $\frac{1}{2}$ wave plate, a Wollaston prism, a $\frac{1}{4}$ wave plate, a Wollaston prism, and convergent lenses in the order listed prior to said flow cell.

19. An apparatus for counting particles suspended in a fluid according to claim 1, wherein said at least one polarizing beam splitter produces a plurality of diverging light beams, and wherein said optical means further includes at least one convergent lens for combining said plurality of diverging light beams to form said irradiation beam.

20. An apparatus for counting particles suspended in a fluid according to claim 2, wherein said at least one polarizing beam splitter produces a plurality of diverging light beams, and wherein said two convergent lenses combine said plurality of diverging light beams to form said irradiation beam.

* * * * *